US011980694B2

(12) United States Patent
Chen et al.

(10) Patent No.: US 11,980,694 B2
(45) Date of Patent: May 14, 2024

(54) STERILIZATION APPARATUS FOR PORTABLE ELECTRONIC DEVICE

(71) Applicants: Yi-Hung Chen, Taipei (TW); Chih-Wen Chiang, Taipei (TW); Yun-Tung Pai, Taipei (TW); Yen-Hua Hsiao, Taipei (TW); Yao-Kuang Su, Taipei (TW); Yi-Hsuan Lin, Taipei (TW); Han-Sheng Siao, Taipei (TW)

(72) Inventors: Yi-Hung Chen, Taipei (TW); Chih-Wen Chiang, Taipei (TW); Yun-Tung Pai, Taipei (TW); Yen-Hua Hsiao, Taipei (TW); Yao-Kuang Su, Taipei (TW); Yi-Hsuan Lin, Taipei (TW); Han-Sheng Siao, Taipei (TW)

(73) Assignee: COMPAL ELECTRONICS, INC., Taipei (TW)

( * ) Notice: Subject to any disclaimer, the term of this patent is extended or adjusted under 35 U.S.C. 154(b) by 584 days.

(21) Appl. No.: 17/319,094

(22) Filed: May 13, 2021

(65) Prior Publication Data

US 2021/0353793 A1 Nov. 18, 2021

Related U.S. Application Data

(60) Provisional application No. 63/026,145, filed on May 18, 2020.

(51) Int. Cl.
*A61L 2/08* (2006.01)
*A61L 2/24* (2006.01)

(52) U.S. Cl.
CPC .............. *A61L 2/084* (2013.01); *A61L 2/24* (2013.01); *A61L 2202/121* (2013.01);
(Continued)

(58) Field of Classification Search
CPC ........ A61L 2/10; A61L 2/08; A61L 2202/122; A61L 2202/16; A61L 2202/121
See application file for complete search history.

(56) References Cited

U.S. PATENT DOCUMENTS

| 2016/0072325 A1* | 3/2016 | Su | H02J 7/0044 |
| | | | 320/114 |
| 2018/0193500 A1 | 7/2018 | Safavi et al. | |

FOREIGN PATENT DOCUMENTS

| CN | 101951004 | 1/2011 |
| CN | 103082901 | 5/2013 |

(Continued)

OTHER PUBLICATIONS

"Office Action of Taiwan Counterpart Application", dated Dec. 15, 2021, p. 1-p. 4.

(Continued)

*Primary Examiner* — Sean E Conley
*Assistant Examiner* — Justin Hwang
(74) *Attorney, Agent, or Firm* — JCIPRNET

(57) ABSTRACT

A sterilization apparatus for a portable electronic device including a cabinet and a carrier is provided. The carrier includes a base slidably disposed on the cabinet, multiple first positioning elements and multiple second positioning elements disposed in parallel on the base, multiple sterilization light sources corresponding to the second positioning elements and multiple pressure sensors disposed in parallel in the base. The base is configured to carry at least one portable electronic device. One second positioning element is disposed between any two adjacent first positioning elements, and any first positioning element and any second positioning element adjacent to each other are separated by a positioning space. The pressure sensors are respectively located in the positioning spaces. One sterilization light source is disposed between any two adjacent pressure sen- (Continued)

sors, and the pressure sensors are configured to sense a pressure from the portable electronic device.

12 Claims, 17 Drawing Sheets

(52) U.S. Cl.
CPC ....... *A61L 2202/14* (2013.01); *A61L 2202/16* (2013.01); *A61L 2202/20* (2013.01)

(56) References Cited

FOREIGN PATENT DOCUMENTS

| | | |
|---|---|---|
| CN | 203632295 | 6/2014 |
| CN | 205007306 | 2/2016 |
| CN | 106820644 | 6/2017 |
| CN | 206389159 | 8/2017 |
| TW | M515229 | 1/2016 |
| TW | M560826 | 6/2018 |

OTHER PUBLICATIONS

"Office Action of China Counterpart Application", dated Sep. 28, 2022, p. 1-p. 10.

* cited by examiner

STERILIZATION APPARATUS FOR PORTABLE ELECTRONIC DEVICE

CROSS-REFERENCE TO RELATED APPLICATION

This application claims the priority benefit of U.S. provisional application Ser. No. 63/026,145, filed on May 18, 2020. The entirety of the above-mentioned patent application is hereby incorporated by reference herein and made a part of this specification.

BACKGROUND

Technical Field

The disclosure relates to a sterilization apparatus, and in particular to a sterilization apparatus for a portable electronic device.

Description of Related Art

Common portable electronic devices, such as a smart phone, a tablet computer, and a laptop, have become indispensable tools in modern life and work because they can send and receive information in real time, process information in real time and are easy to carry around. Viruses or bacteria in the surrounding environment may attach to the above portable electronic devices and invade the human body. With the increase of health awareness, relevant manufacturers have developed sterilization apparatus for the above portable electronic devices, so that users can disinfect and sterilize the above portable electronic devices at any time or at regular intervals.

Common sterilization apparatus includes a sterilization box, a tray, and a sterilization light source. To disinfect and sterilize a laptop, for example, the user needs to first place the laptop on the tray, then send the tray into the sterilization box, and finally, the sterilization light source inside the sterilization box emits the sterilization light and irradiates the exterior surface of the laptop to complete the disinfection and sterilization. However, the touchpad, the keyboard, and the display surface of the display frequently touched by the user are not exposed to the sterilization light emitted by the sterilization light source, so there is a risk of virus or bacteria residue. On the other hand, during the sterilization process, all the sterilization light sources in the sterilization box will be activated, and it is not possible to activate specific sterilization light source according to the position of the laptop on the tray or the number of laptops, which not only lacks flexibility in terms of operation and consumes a lot of electricity, but also tends to reduce the sterilization effectiveness.

SUMMARY

The disclosure provides a sterilization apparatus for a portable electronic device, which can not only disinfect and sterilize comprehensively the portable electronic device, but also has excellent flexibility and safety in terms of operation.

The disclosure proposes a sterilization apparatus for a portable electronic device, which includes a cabinet and at least one carrier. The carrier includes a base, multiple first positioning elements disposed in parallel on the base, multiple second positioning elements disposed in parallel on the base, multiple sterilization light sources, and multiple pressure sensors. The base is slidably disposed on the cabinet and configured to carry at least one portable electronic device. One of the second positioning elements is disposed between any two of the first positioning elements adjacent to each other, and any one of the first positioning elements is separated from any one of the second positioning elements by a positioning space. The sterilization light sources disposed correspondingly to the second positioning elements. The pressure sensors are disposed in parallel in the base. The pressure sensors are respectively located in the positioning spaces, and one if the sterilization light sources is disposed between any two of the pressure sensors adjacent to each other. When the portable electronic device is put into any one of the positioning spaces, and the pressure sensor located in the positioning space senses a pressure from the portable electronic device, the sterilization light source adjacent to the pressure sensor switches to a preparatory starting status.

According to an embodiment of the disclosure, a height of each of the first positioning elements is lower than a height of each of the second positioning elements.

According to an embodiment of the disclosure, the each of the second positioning elements includes a substrate connected to the base and a light transmitting cover disposed on the substrate. The sterilization light sources are respectively disposed on the substrates, and are respectively covered by the light transmitting covers.

According to an embodiment of the disclosure, the each of the second positioning elements includes a substrate connected to the base and a light transmitting plate disposed on the substrate. The sterilization light sources are respectively disposed on the substrates, and are respectively clamped between the light transmitting plates and the substrates.

According to an embodiment of the disclosure, the substrate of the each of the second positioning elements has a groove, and the sterilization light source and the light transmitting plate are disposed in the groove.

According to an embodiment of the disclosure, a top end of the light transmitting plate of the each of the second positioning elements is lower than or a same height as a top end of the substrate.

According to an embodiment of the disclosure, a top end of the light transmitting plate of the each of the second positioning elements is higher than a top end of the substrate.

According to an embodiment of the disclosure, the each of the second positioning elements includes a substrate connected to the base and a light transmitting plate disposed on the substrate, and the sterilization light source is disposed on a top end of the light transmitting plate.

According to an embodiment of the disclosure, each of the sterilization light sources is disposed on a side of a corresponding second positioning element far away from the base, and a top end of the each of the sterilization light sources is a same height as or higher than a top end of the corresponding second positioning element.

According to an embodiment of the disclosure, the each of the second positioning elements includes a connecting portion connected to the base and a positioning portion connected to the connecting portion, and the positioning portion of the each of the second positioning elements is suspended on the base. The sterilization light sources are disposed on the base, and orthographic projection of the positioning portions of the second positioning elements on the base respectively overlaps the sterilization light sources.

According to an embodiment of the disclosure, the base includes a main body portion and a light transmitting portion disposed on the main body portion. The connecting portion of the each of the second positioning elements is connected to the main body portion, and the first positioning elements are disposed in parallel on the light transmitting portion. The sterilization light sources are disposed in the main body portion and covered by the light transmitting portion.

According to an embodiment of the disclosure, the sterilization apparatus for a portable electronic device further includes a door panel. The door panel is movably connected to the cabinet. When the carrier is moved into the cabinet and the door panel is locked to the cabinet, the sterilization light source in the preparatory starting status is activated to emit a sterilization light.

Based on the above, in the sterilization apparatus of the disclosure, the carrier has multiple positioning spaces arranged alternately for carrying and positioning multiple portable electronic devices, so that each part of each of the portable electronic devices may be completely sterilized. In addition, the carrier integrates an auto-sensing sterilization mechanism, which can sense the position of the each of the portable electronic devices on the carrier, and control a specific sterilization light source (for example: the sterilization light source closest to the portable electronic device) to enter the preparatory starting status. Once the sterilization apparatus switches from an on state to an off state, the specific sterilization light source is immediately activated. Therefore, the sterilization apparatus of the disclosure not only has excellent flexibility in terms of operation, but also improves sterilization effectiveness and saves energy. In addition, the auto-sensing sterilization mechanism can prevent the sterilization light emitted by the sterilization light source from irradiating the surrounding personnel, thereby improving safety in terms of operation.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1A:
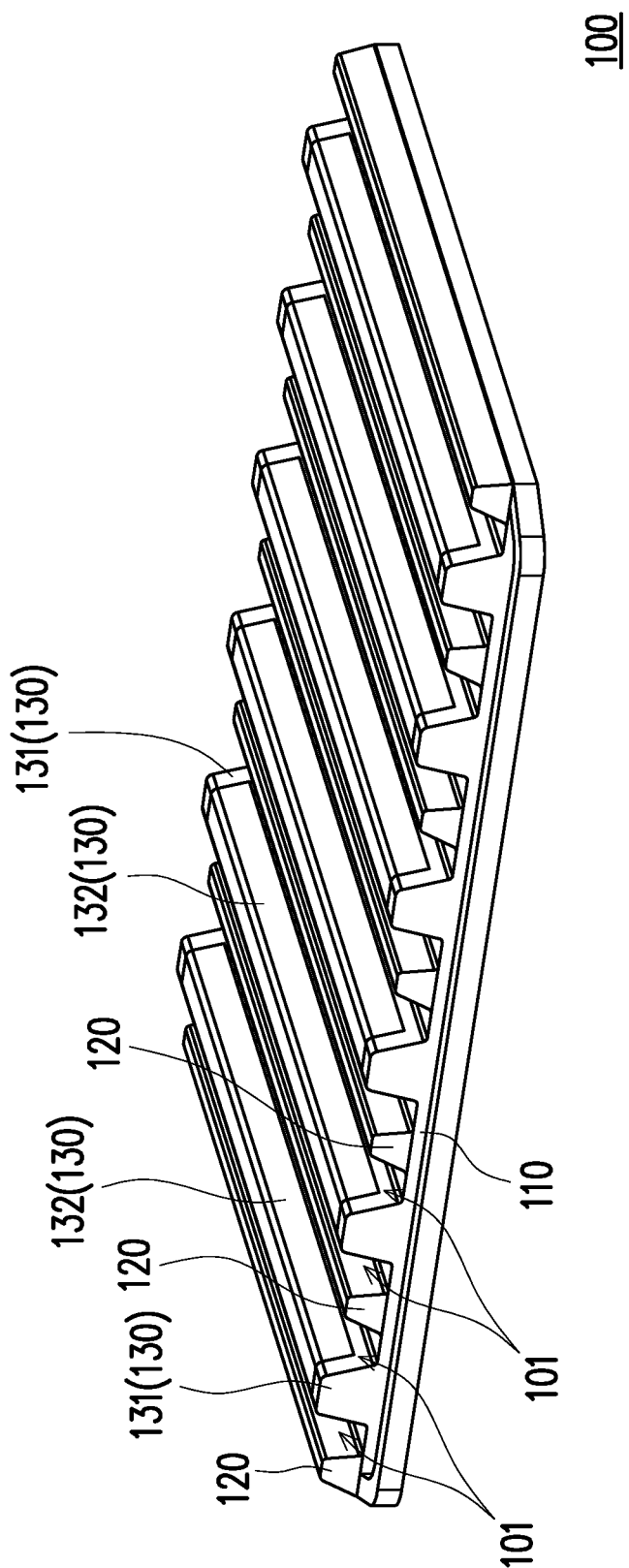
FIG. 1A is a schematic view of a carrier according to a first embodiment of the disclosure.
Figure 1B:
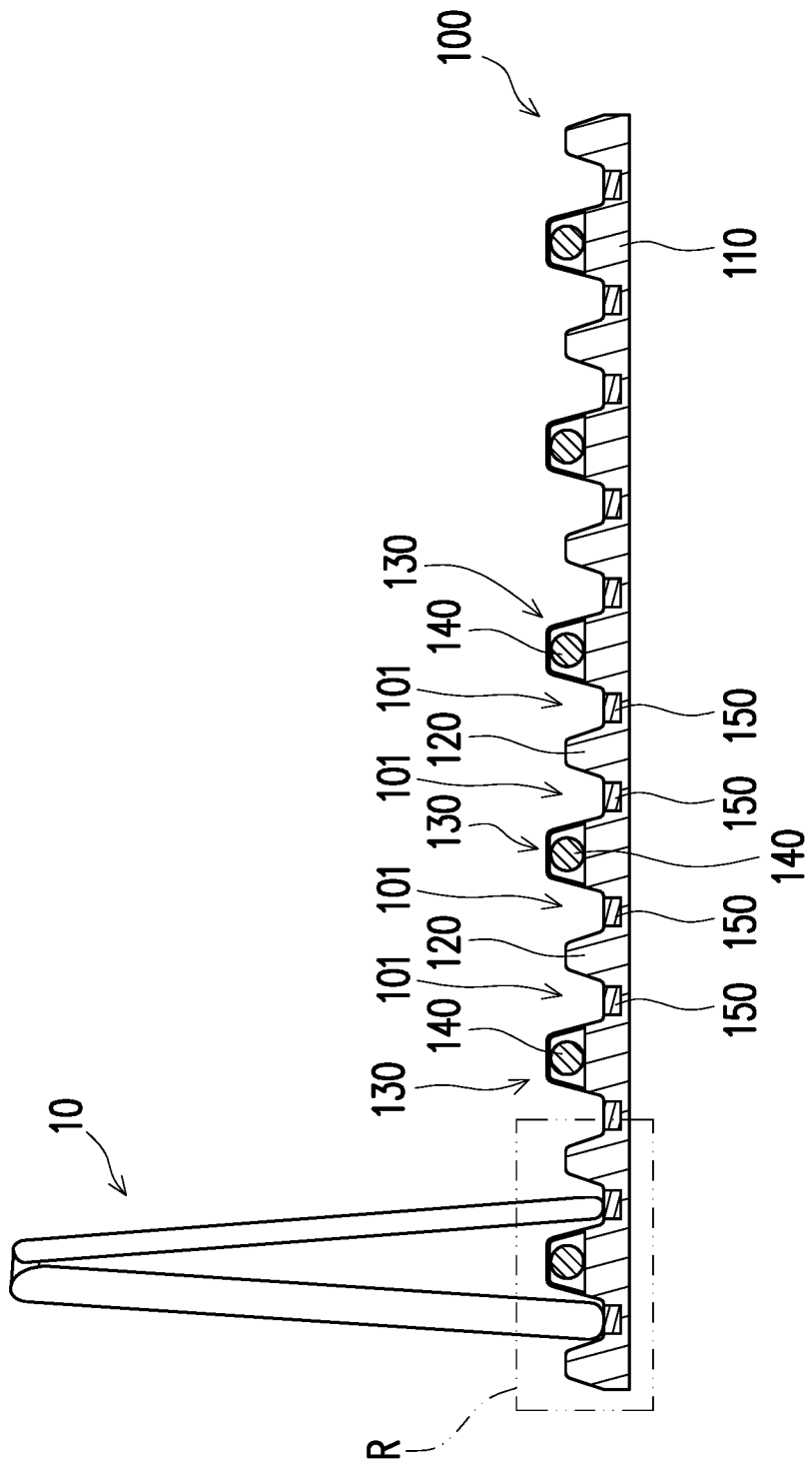
FIG. 1B is a schematic cross-sectional view of the carrier in FIG. 1A.
Figure 1C:
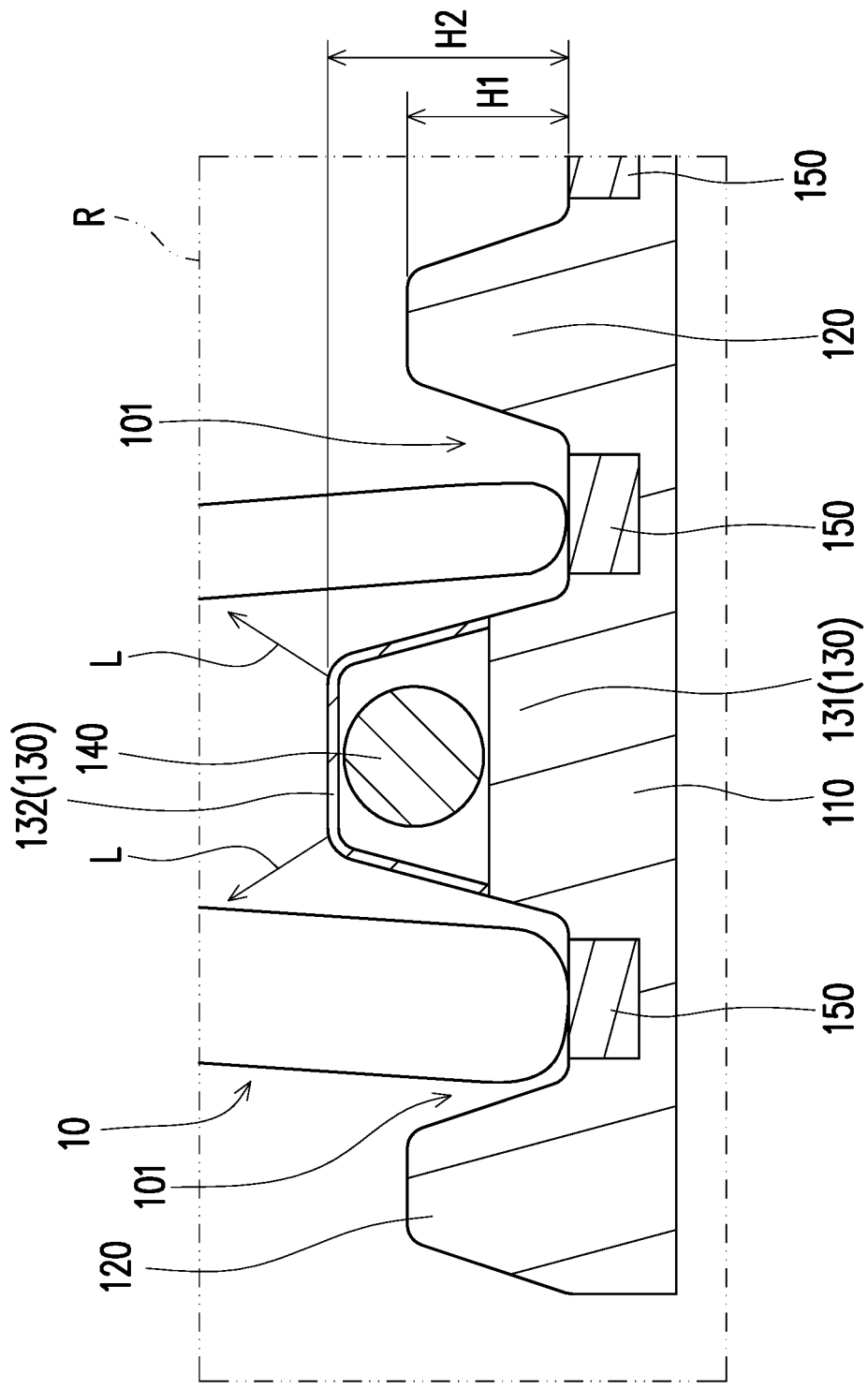
FIG. 1C is an enlarged schematic view of a region R in FIG. 1B.

FIG. 1A is a schematic view of a carrier according to a first embodiment of the disclosure. FIG. 1B is a schematic cross-sectional view of the carrier in FIG. 1A. FIG. 1C is an enlarged schematic view of a region R in FIG. 1B. Referring to FIG. 1A to FIG. 1C, in this embodiment, a carrier 100 may carry a or multiple portable electronic devices 10, and a laptop is used as an example, but is not limited thereto. For example, the portable electronic device 10 may also be a smart phone, a tablet computer, or other electronic products that can be carried around.

In detail, the carrier 100 includes a base 110, multiple first positioning elements 120 disposed in parallel on the base 110, multiple second positioning elements 130 disposed in parallel on the base 110, multiple sterilization light sources 140, and multiple pressure sensors 150. The first positioning elements 120 and the second positioning elements 130 are alternately arranged, and one of the second positioning elements 130 is disposed between any two of the first positioning elements 120 adjacent to each other. In other words, any two of the first positioning elements 120 adjacent to each other are separated by one of the second positioning elements 130. In addition, a distance is maintained between any one of the first positioning elements 120 and any one of the second positioning elements 130 adjacent to each other to define a positioning space 101 of the portable electronic device 10. In other words, any one of the first positioning elements 120 and any one of the second positioning elements 130 adjacent to each other are separated by one positioning space 101.

One sterilization light source 140 is disposed in each of the second positioning elements 130, and one sterilization light source 140 is disposed between any two of the first positioning elements 120 adjacent to each other or between any two of the positioning spaces 101 adjacent to each other. In detail, the each of the second positioning elements 130 includes a substrate 131 connected to the base 110 and a light transmitting cover 132 disposed on the substrate 131. Each of the sterilization light sources 140 is disposed on a corresponding substrate 131 and is covered by a corresponding light transmitting cover 132 to improve brightness and homogeneity of light. In addition, a protruding height H1 of each of the first positioning elements 120 on the base 110 is lower than a protruding height H2 of the second positioning element 130 on the base 110 to guide the user to install and position the portable electronic device 10 on the base 110, or to be as an identification mechanism when installing and positioning the portable electronic device 10.

As shown in FIG. 1C, two bodies of the portable electronic device 10 are respectively put into two positioning spaces 101 adjacent to each other, and are separated by the second positioning element 130. A sterilization light L emitted by the sterilization light source 140 may pass through the light transmitting cover 132 to illuminate the two bodies of the portable electronic device 10, and illuminate a touchpad, a keyboard, and a display surface of a display to disinfect and sterilize comprehensively the portable electronic device 10.

Referring to FIG. 1B and FIG. 1C, one pressure sensor 150 is disposed in each of the positioning spaces 101, or in other words, one pressure sensor 150 is disposed between any one of the first positioning elements 120 and any one of the second positioning elements 130 adjacent to each other, or in other words, any two of the pressure sensors 150 adjacent to each other are separated by one of the first positioning elements 120 or one of the second positioning element 130. Furthermore, the pressure sensors 150 are disposed in parallel in the base 110. Orthographic projection of the first positioning elements 120 on the base 110, orthographic projection of the second positioning elements 130 on the base 110, and orthographic projection of the pressure sensors 150 on the base 110 does not overlap with each other.

In this embodiment, the carrier 100 integrates an auto-sensing sterilization mechanism, and is mainly composed of the sterilization light sources 140 and the pressure sensors 150. Specifically, one of the sterilization light sources 140 is disposed between any two of the pressure sensors 150 adjacent to each other, and they are disposed in groups. When the portable electronic device 10 is put into any one of the positioning spaces 101, and the pressure sensor 150 located in the positioning space 101 senses a weight or a pressure from the portable electronic device 10, the sterilization light source 140 adjacent to or closest to the pressure sensor 150 switches to a preparatory starting status. The preparatory starting status means that a controller or a processor (not shown) receives a signal from the pressure sensor 150 and determines a position of the portable electronic device 10 on the carrier 100, later, when the controller or the processor (not shown) receives a trigger signal, a specific one of the sterilization light sources 140 will be activated immediately (for example: the sterilization light source 140 closest to the portable electronic device 10), rather than all the sterilization light sources 140 will be activated immediately when the portable electronic device 10 is placed on the carrier 100.

Therefore, the auto-sensing sterilization mechanism not only improves flexibility in terms of operation, but also improves sterilization effectiveness and saves energy. In addition, the auto-sensing sterilization mechanism can prevent the sterilization light L emitted by the sterilization light source 140 from irradiating the surrounding personnel, thereby improving safety in terms of operation.

Figure 2A:
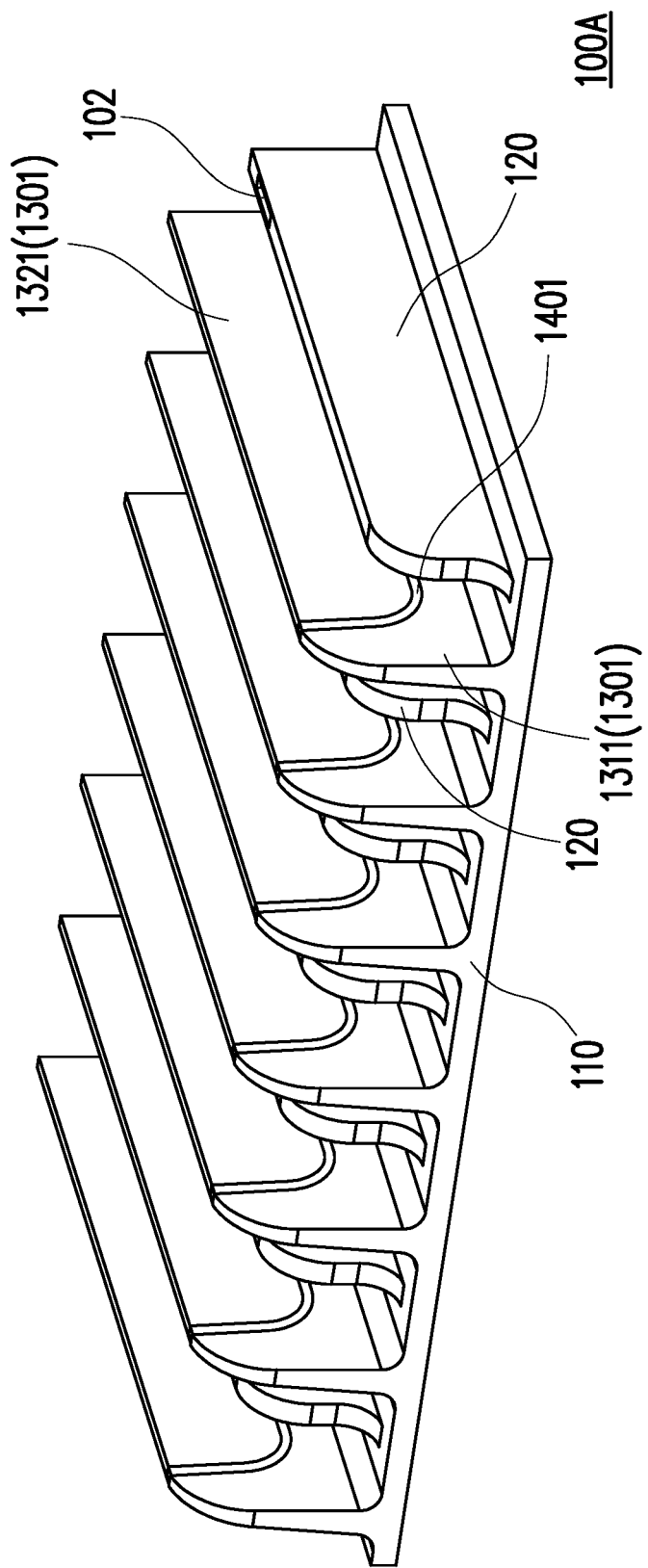
FIG. 2A is a schematic view of a carrier according to a second embodiment of the disclosure.
Figure 2B:
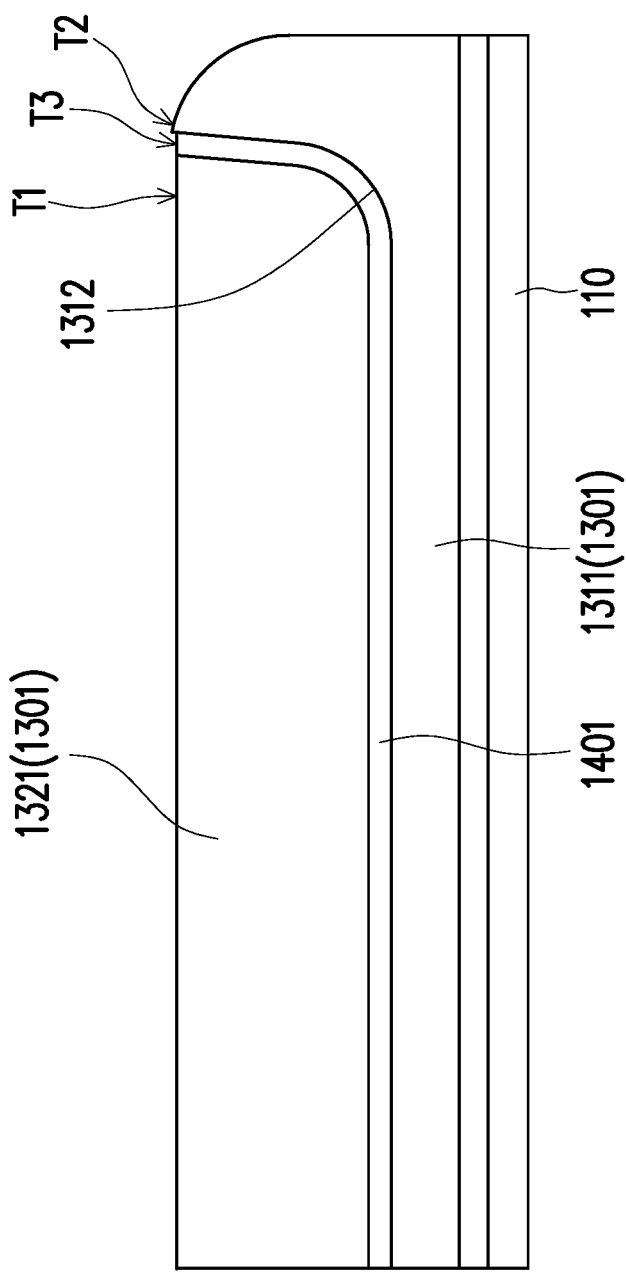
FIG. 2B is a schematic side view of the carrier in FIG. 2A.
Figure 2C:
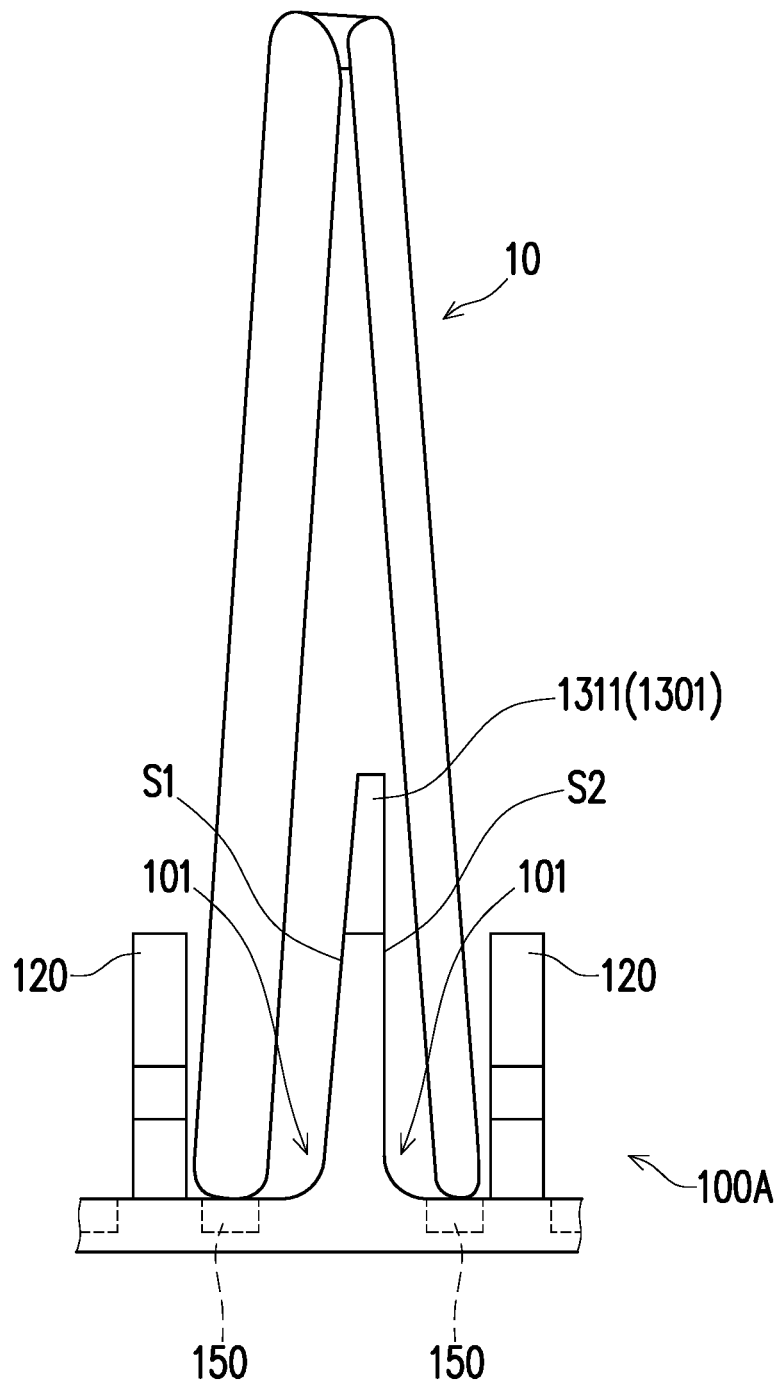
FIG. 2C is a partial schematic front view of the carrier in FIG. 2A.

FIG. 2A is a schematic view of a carrier according to a second embodiment of the disclosure. FIG. 2B is a schematic side view of the carrier in FIG. 2A. FIG. 2C is a partial schematic front view of the carrier in FIG. 2A. Referring to FIG. 2A to FIG. 2C, a carrier 100A according to this embodiment is substantially the same design as the carrier 100 according to the first embodiment. The main difference lies in the design of the second positioning elements. In this embodiment, each of second positioning elements 1301 includes a substrate 1311 connected to the base 110 and a light transmitting plate 1321 disposed on the substrate 1311. Each of sterilization light sources 1401 is disposed on the substrate 1311 of a corresponding second positioning element 1301, and is clamped between the light transmitting plate 1321 of the second positioning element 1301 and the substrate 1311 corresponding to each other.

As shown in FIG. 2B, a top end T1 of the light transmitting plate 1321 may be lower than a top end T2 of the substrate 1311. The sterilization light source 1401 may be a light strip clamped between the light transmitting plate 1321 and the substrate 1311, and the light transmitting plate 1321 helps to improve brightness and homogeneity of light. In addition, the sterilization light source 1401 has a top end T3 exposed between the top end T1 of the light transmitting plate 1321 and the top end T2 of the substrate 1311, and the top end T3 may be a same height as the top end T1 of the light transmitting plate 1321. In other embodiments, the top end T1 of the light transmitting plate 1321 may be a same height as the top end T2 of the substrate 1311.

As shown in FIG. 2C, the second positioning element 1301 has a first side surface S1 facing an adjacent first positioning element 120 and a second side surface S2 facing another adjacent first positioning element 120. The first side surface S1 may be an inclined plane, and the second side surface S2 may be a vertical plane. Furthermore, compared to the positioning space 101 adjacent to the second side surface S2, the positioning space 101 adjacent to the first side surface S1 presents as an inclined geometry to provide a larger placement space. For example, a thickness of a left system end of the portable electronic device 10 is significantly greater than a thickness of a right screen end. The positioning space 101 adjacent to the first side surface S1 may provide enough space to accommodate the left system end of the portable electronic device 10.

As shown in FIG. 2A, a top surface of the each of the first positioning elements 120 may be provided with an electrical connection slot 102 for the portable electronic device 10 to be electrically connected to the electrical connection slot 102 through an electrical connector to charge. As shown in FIG. 2B, the substrate 1311 has a groove 1312, and the sterilization light source 1401 and the light transmitting plate 1321 are disposed in the groove 1312 to improve structural integration.

Figure 3:
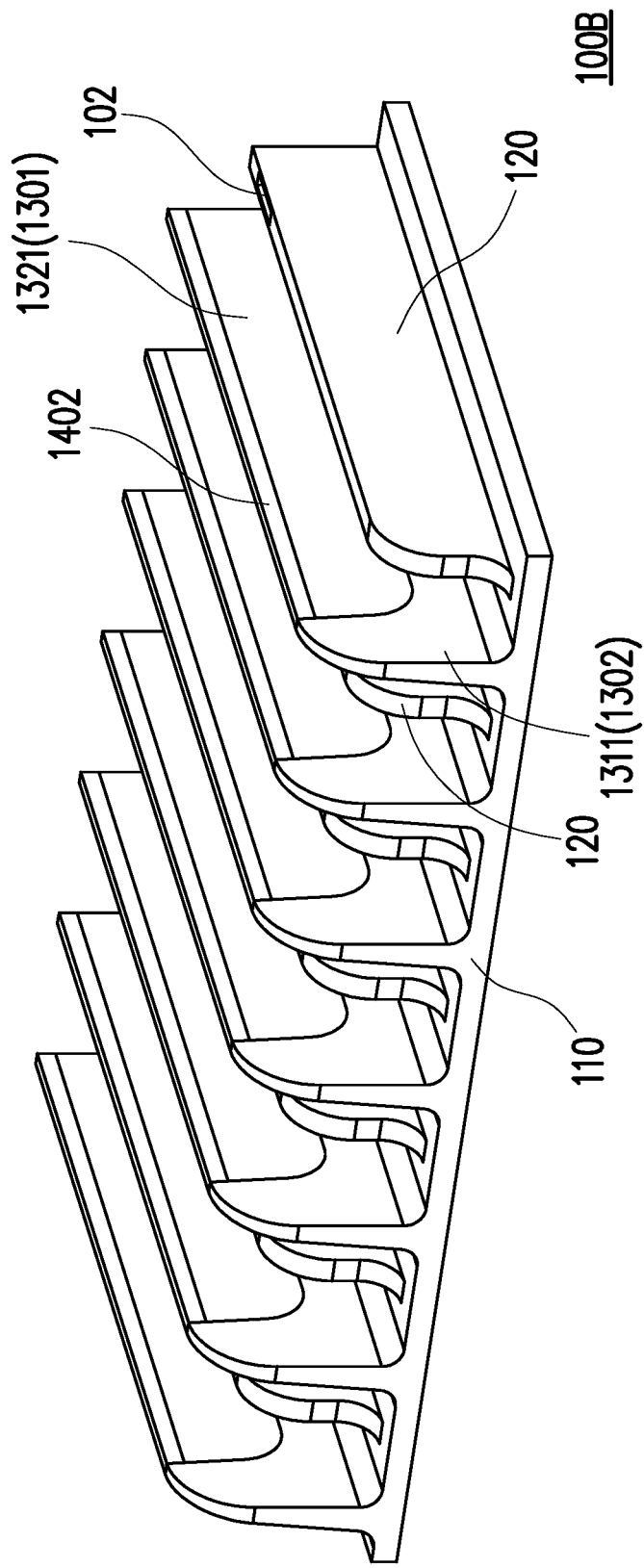
FIG. 3 is a schematic view of a carrier according to a third embodiment of the disclosure.

FIG. 3 is a schematic view of a carrier according to a third embodiment of the disclosure. Referring to FIG. 3, a carrier 100B of this embodiment is substantially the same design as the carrier 100A of the second embodiment. The main difference lies in the position of the sterilization light source. In this embodiment, the light transmitting plate 1321 of the second positioning element 1302 is disposed on the substrate 1311. A sterilization light source 1402 may be in a form of a light strip or a light tube, for example, and is disposed on a top end of the light transmitting plate 1321.

Figure 4A:
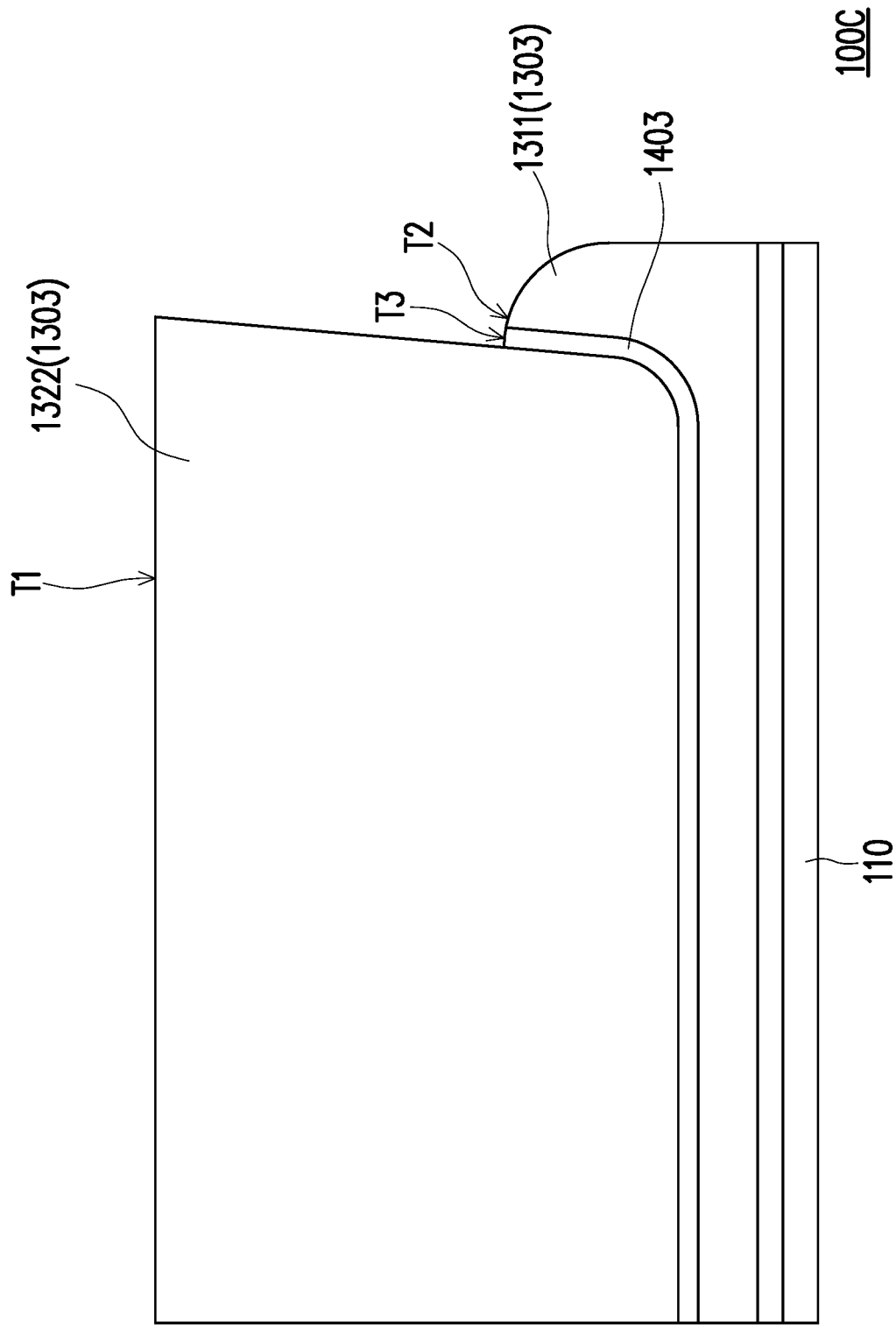
FIG. 4A is a schematic view of a carrier according to a fourth embodiment of the disclosure.
Figure 4B:
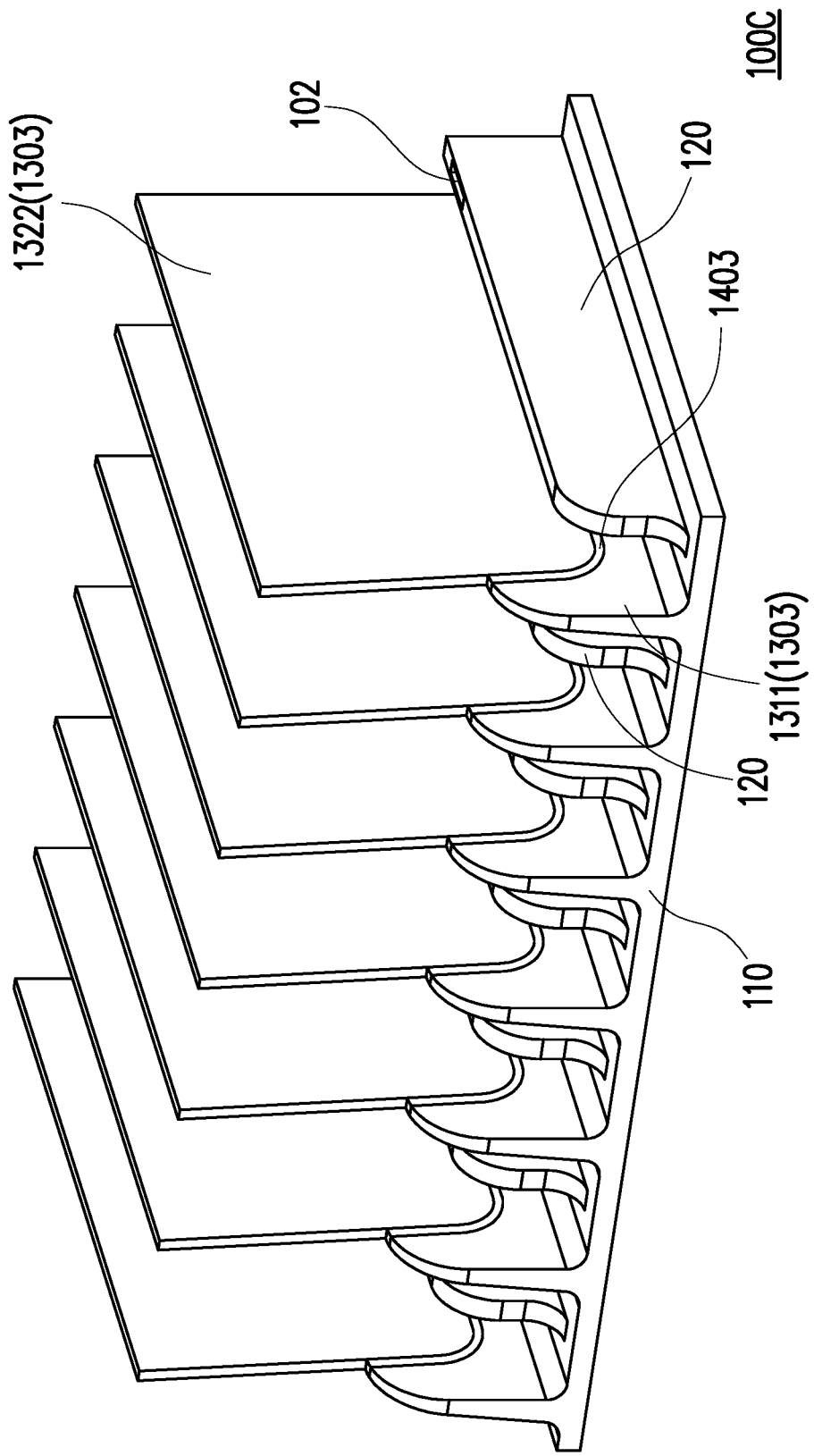
FIG. 4B is a schematic side view of the carrier in FIG. 4A.

FIG. 4A is a schematic view of a carrier according to a fourth embodiment of the disclosure. FIG. 4B is a schematic side view of the carrier in FIG. 4A. Referring to FIG. 4A and FIG. 4B, a carrier 100C of this embodiment is substantially the same design as the carrier 100A of the second embodiment. The main difference lies in the structural design of the light transmitting plate. In this embodiment, the top end T1 of the light transmitting plate 1321 of a second positioning element 1303 is higher than the top end T2 of the substrate 1311 and the top end T3 of a sterilization light source 1403 to increase illumination range.

Figure 5:
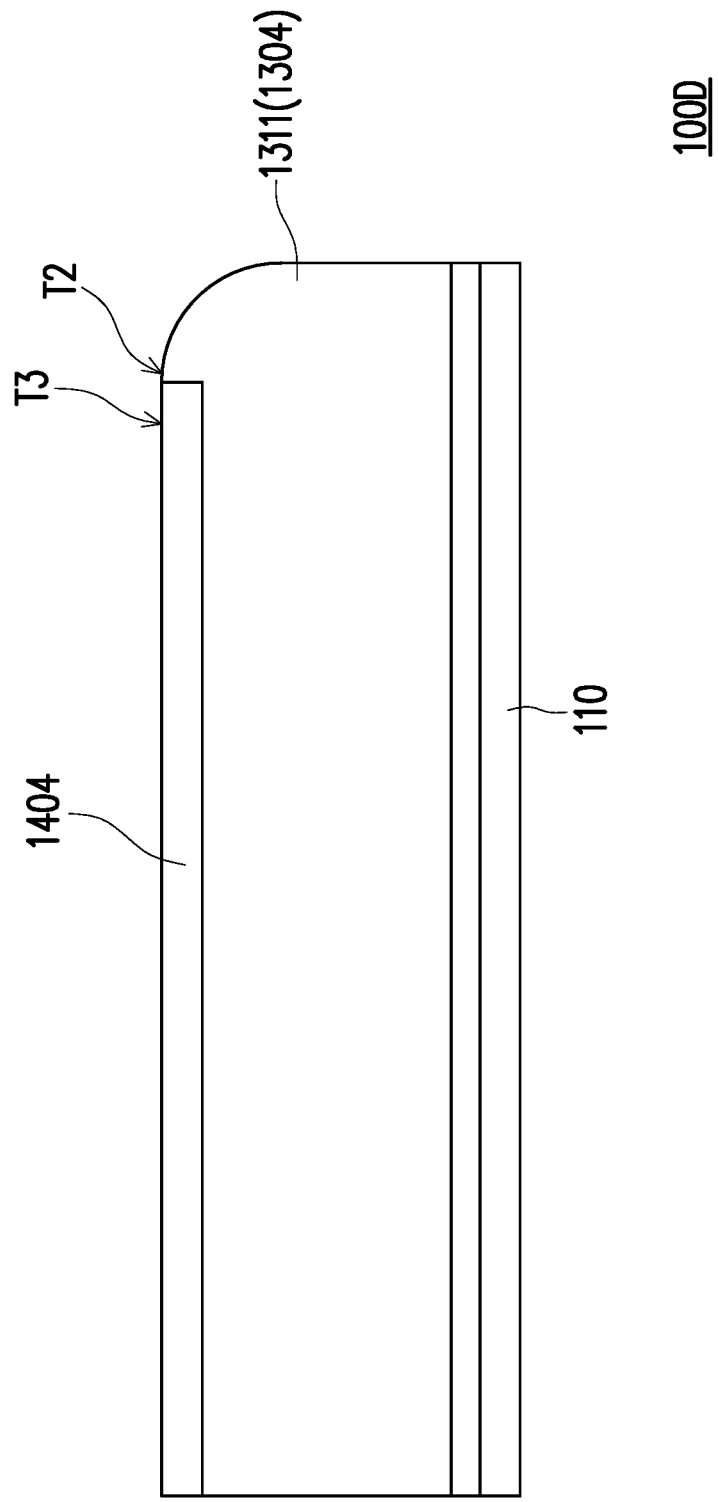
FIG. 5 is a schematic side view of a carrier according to a fifth embodiment of the disclosure.

FIG. 5 is a schematic side view of a carrier according to a fifth embodiment of the disclosure. Referring to FIG. 5, a carrier 100D of this embodiment is substantially the same design as the carrier 100B of the third embodiment. The main difference is that in this embodiment, a second positioning element 1304 does not have a light transmitting plate, and a sterilization light source 1404 is disposed on a side of the substrate 1311 away from the base 110. In addition, the top end T3 of the sterilization light source 1404 may be a same height as the top end T2 of the substrate 1311.

In other embodiments, the top end T3 of the sterilization light source 1404 may be higher than the top end T2 of the substrate 1311.

Figure 6A:
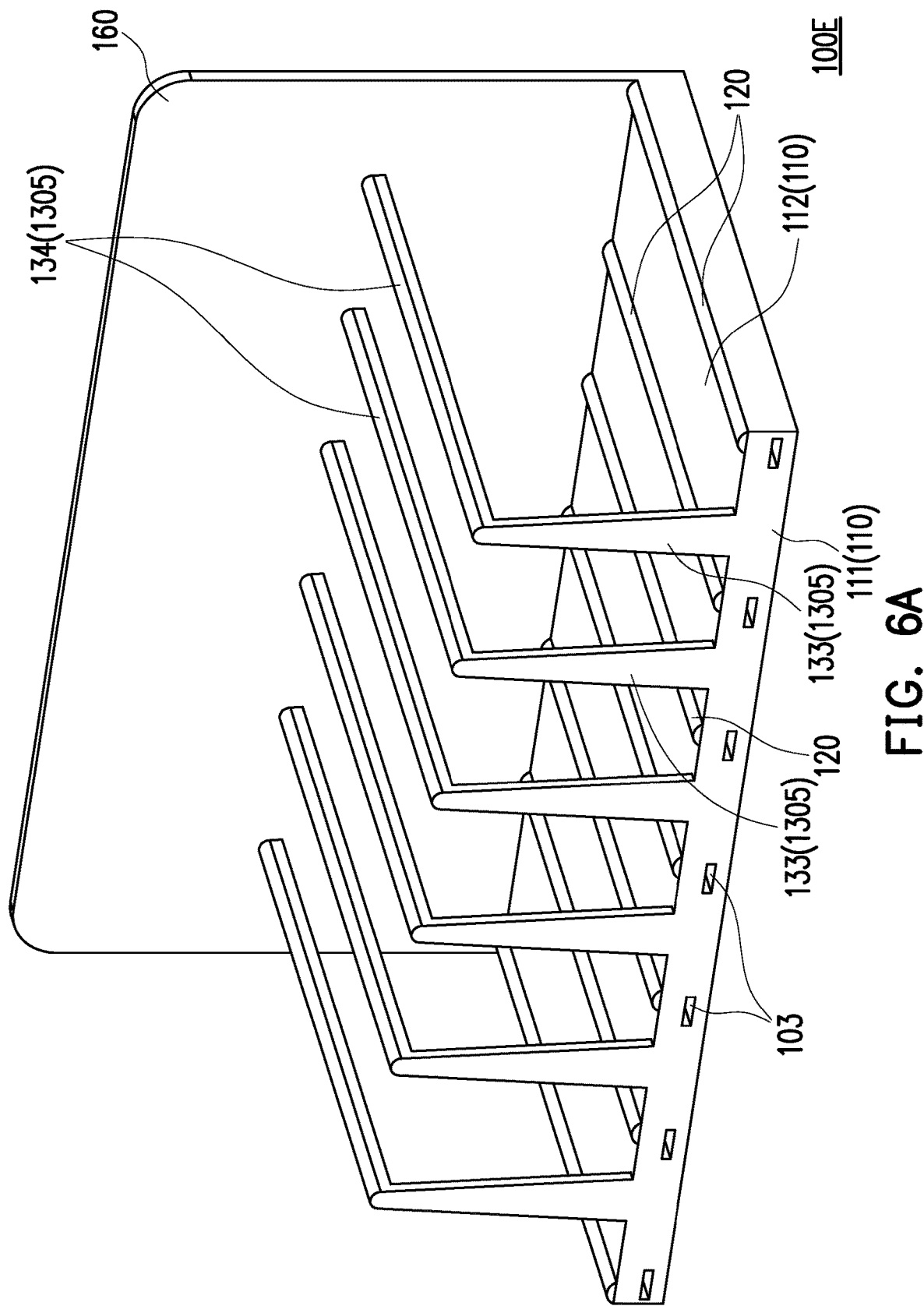
FIG. 6A is a schematic view of a carrier according to a sixth embodiment of the disclosure.
Figure 6B:
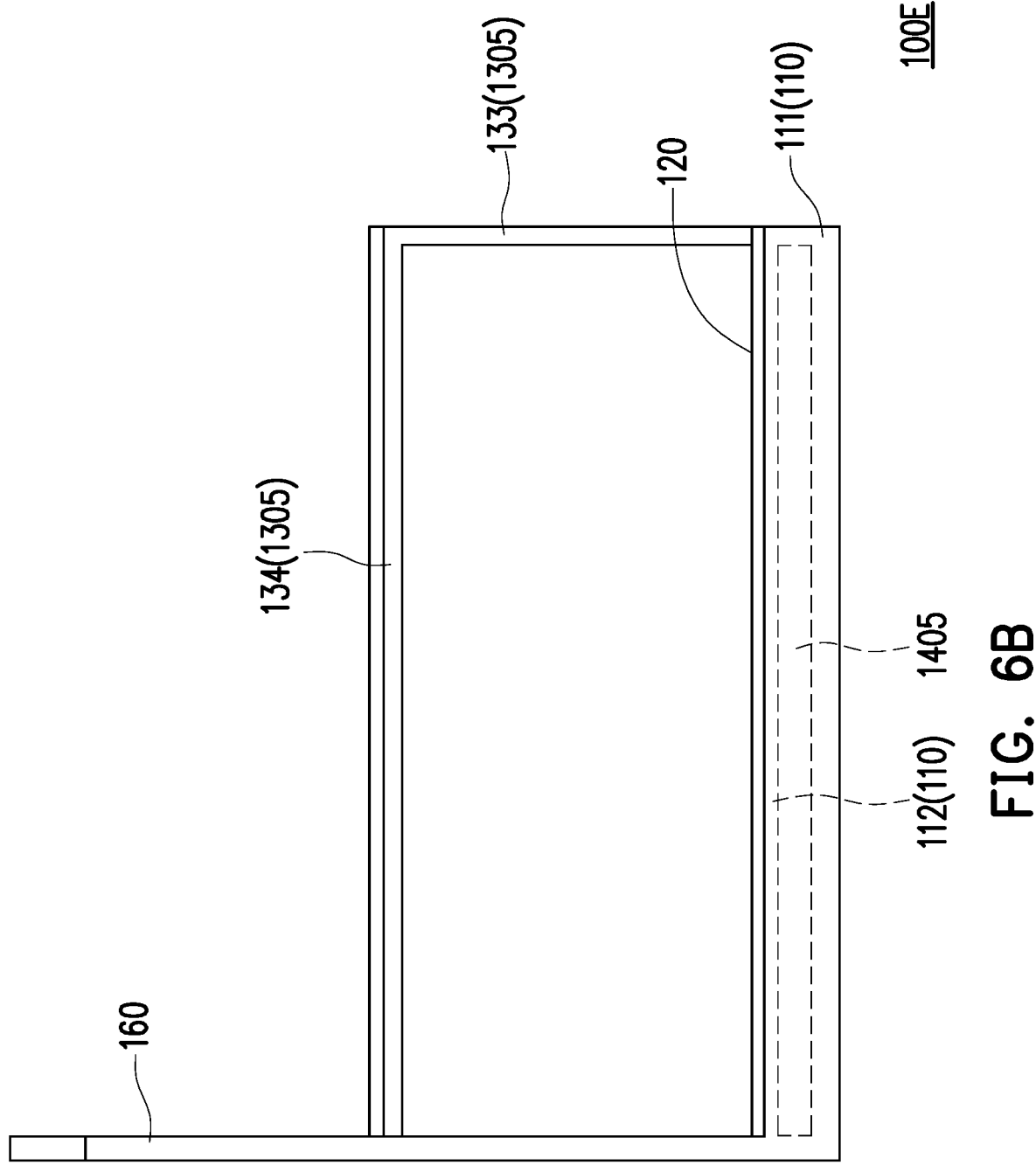
FIG. 6B is a schematic side view of the carrier of FIG. 6A.
Figure 6C:
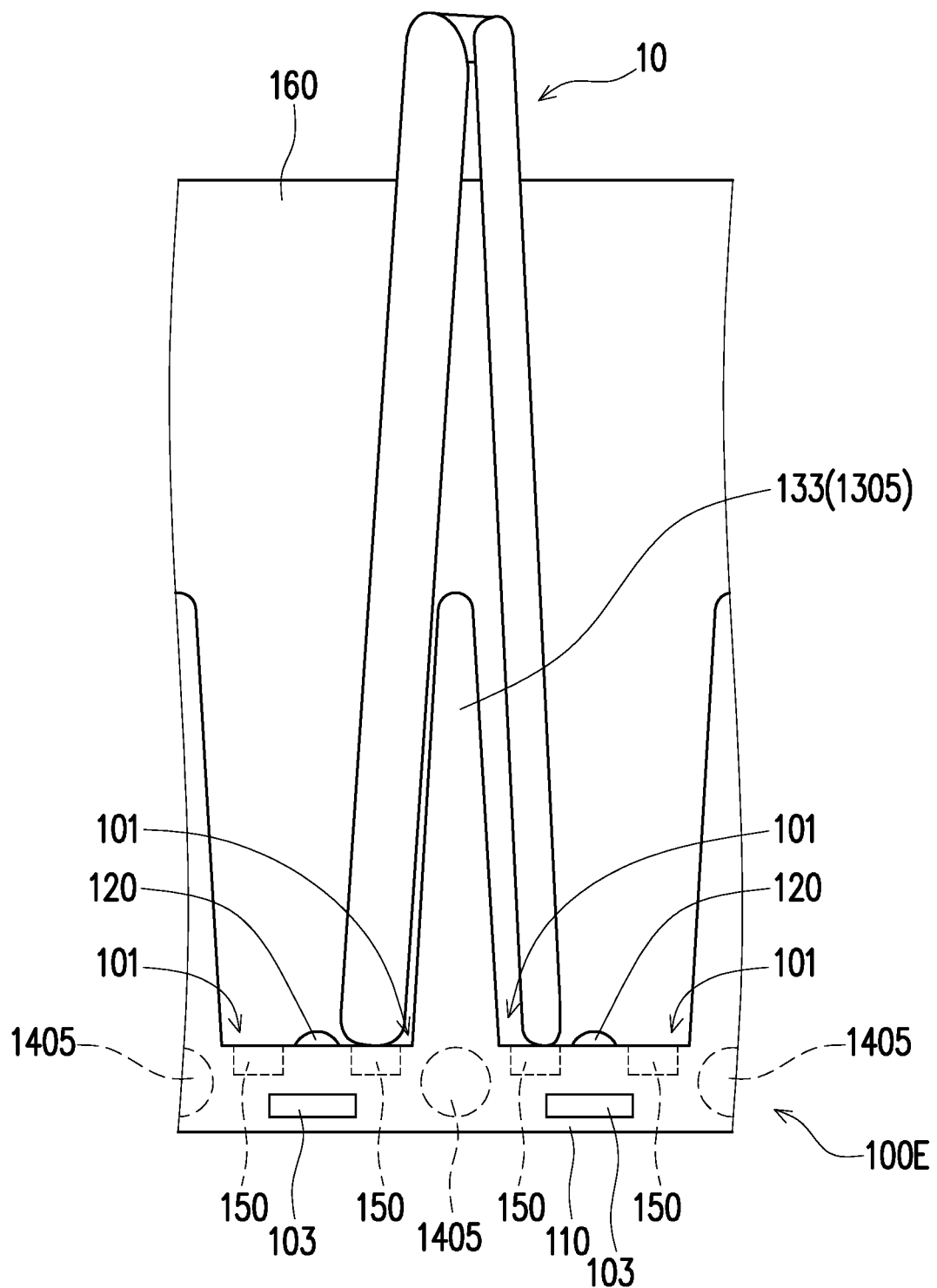
FIG. 6C is a schematic partial front view of the carrier of FIG. 6A.

FIG. 6A is a schematic view of a carrier according to a sixth embodiment of the disclosure. FIG. 6B is a schematic side view of the carrier of FIG. 6A. FIG. 6C is a schematic partial front view of the carrier of FIG. 6A. Referring to FIG. 6A to FIG. 6C, a carrier 100E of this embodiment is substantially the same design as the carrier 100 of the first embodiment. The main difference lies in the design of the second positioning elements. In this embodiment, each of second positioning elements 1305 includes a connecting portion 133 connected to the base 110 and a positioning portion 134 connected to the connecting portion 133. Each of the positioning portions 134 is suspended from the base 110 and may be perpendicular to a corresponding connecting portion 133.

The carrier 100E also has a side wall 160 relative to the connecting portion 133 of each of the second positioning elements 1305. The connecting portion 133 of the each of the second positioning elements 1305 protrudes from one side of the base 110, and the side wall 160 protrudes from another side of the base 110. The positioning portion 134 extends from the connecting portion 133 to the side wall 160 and may contact the side wall 160.

As shown in FIG. 6B and FIG. 6C, multiple sterilization light sources 1405 are disposed on the base 110, and orthographic projection of the positioning portions 134 of the second positioning elements 1305 on the base 110 overlaps with the sterilization light sources 1405. In addition, an extension direction of the each of the positioning portions 134 is parallel to an extension direction of a corresponding sterilization light source 1405.

As shown in FIG. 6A to FIG. 6C, the base 110 includes a main body portion 111 and a light transmitting portion 112 disposed on the main body portion 111. The connecting portion 133 of the each of the second positioning elements 1305 is connected to the main body portion 111, and the first positioning elements 120 are disposed in parallel on the light transmitting portion 112. In addition, the sterilization light sources 1405 are disposed in the main body portion 111 and covered by the light transmitting portion 112 to improve brightness, diffusivity, and homogeneity of light.

As shown in FIG. 6A and FIG. 6C, a side wall surface of the base 110 is provided with multiple electrical connection slots 103 for the portable electronic device 10 to be electrically connected to the electrical connection slot 103 through an electrical connector to charge.

Figure 7A:
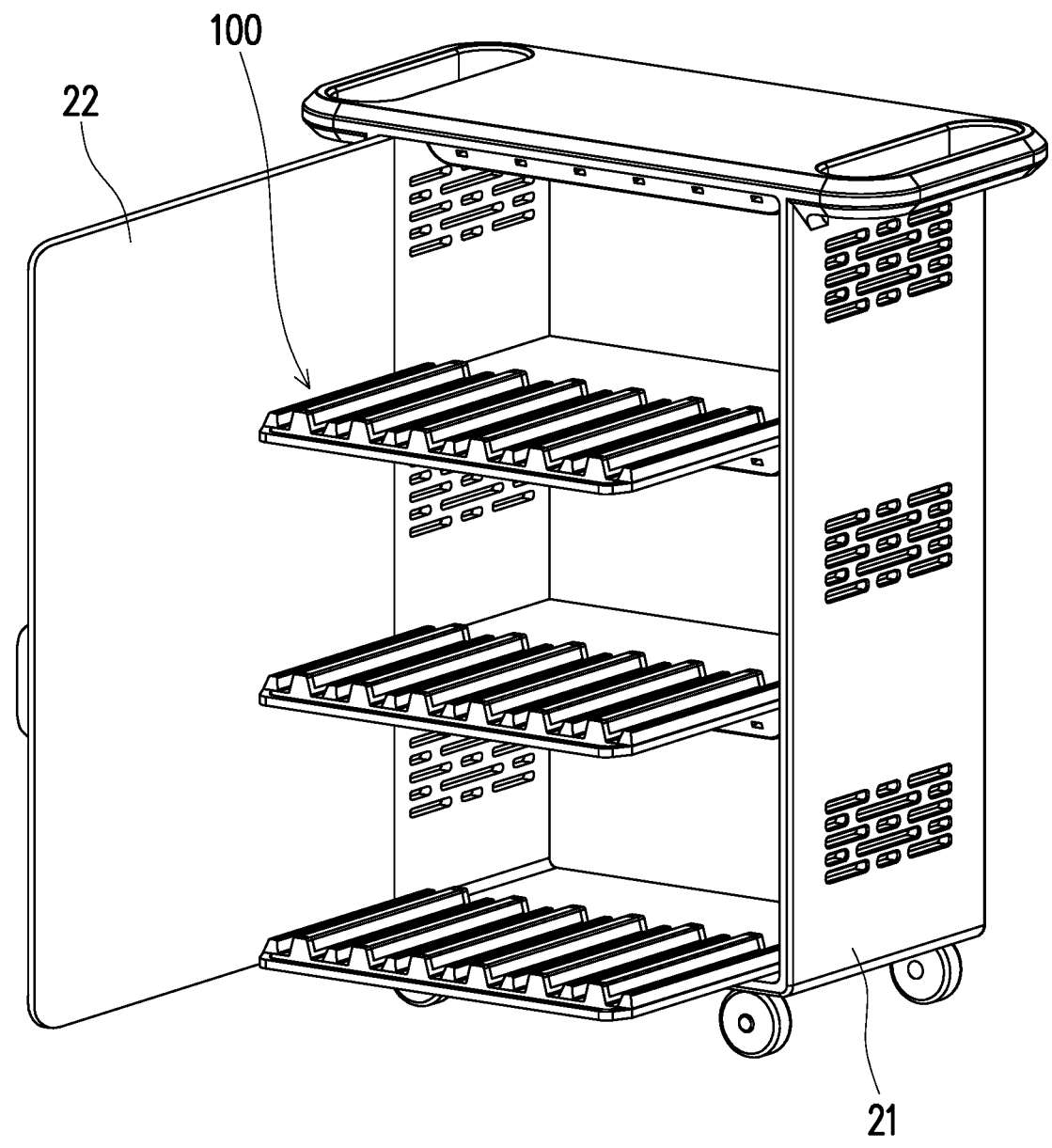
FIG. 7A and FIG. 7B are schematic views of a sterilization apparatus according to an embodiment of the disclosure in a state where a door is open.
Figure 7B:
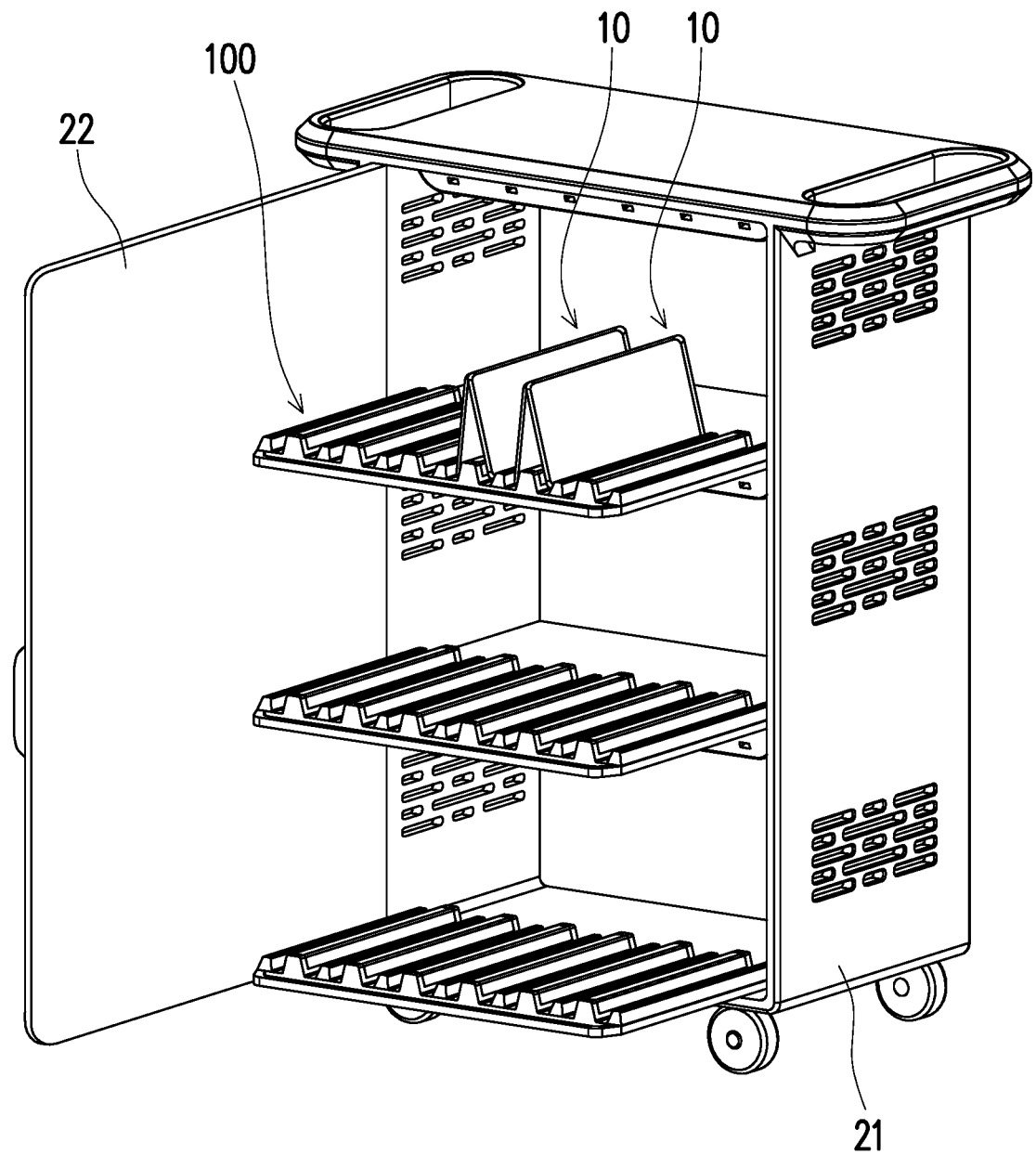
Figure 7C:
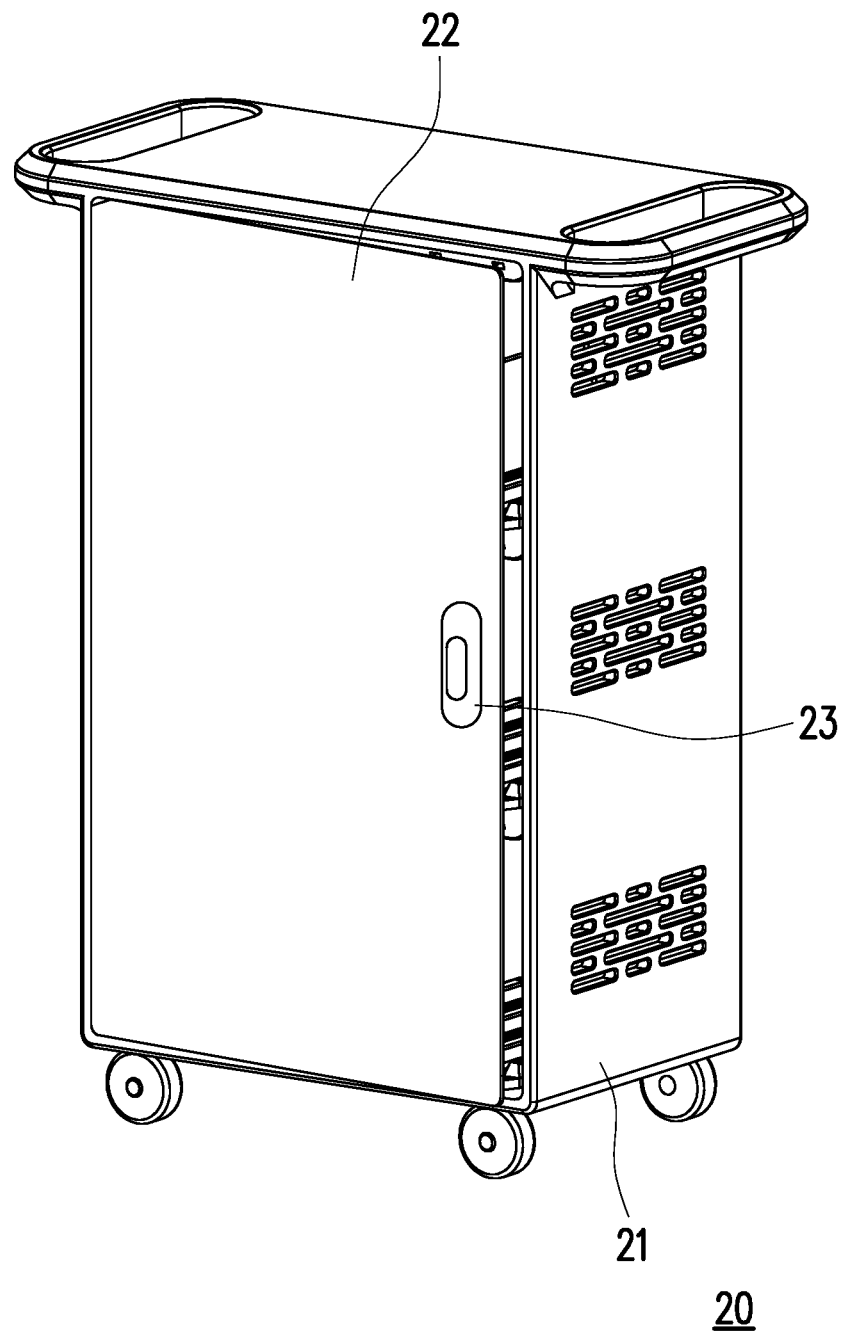
FIG. 7C is a schematic view of a sterilization apparatus according to an embodiment of the disclosure in a state where a door is not completely closed.
Figure 7D:
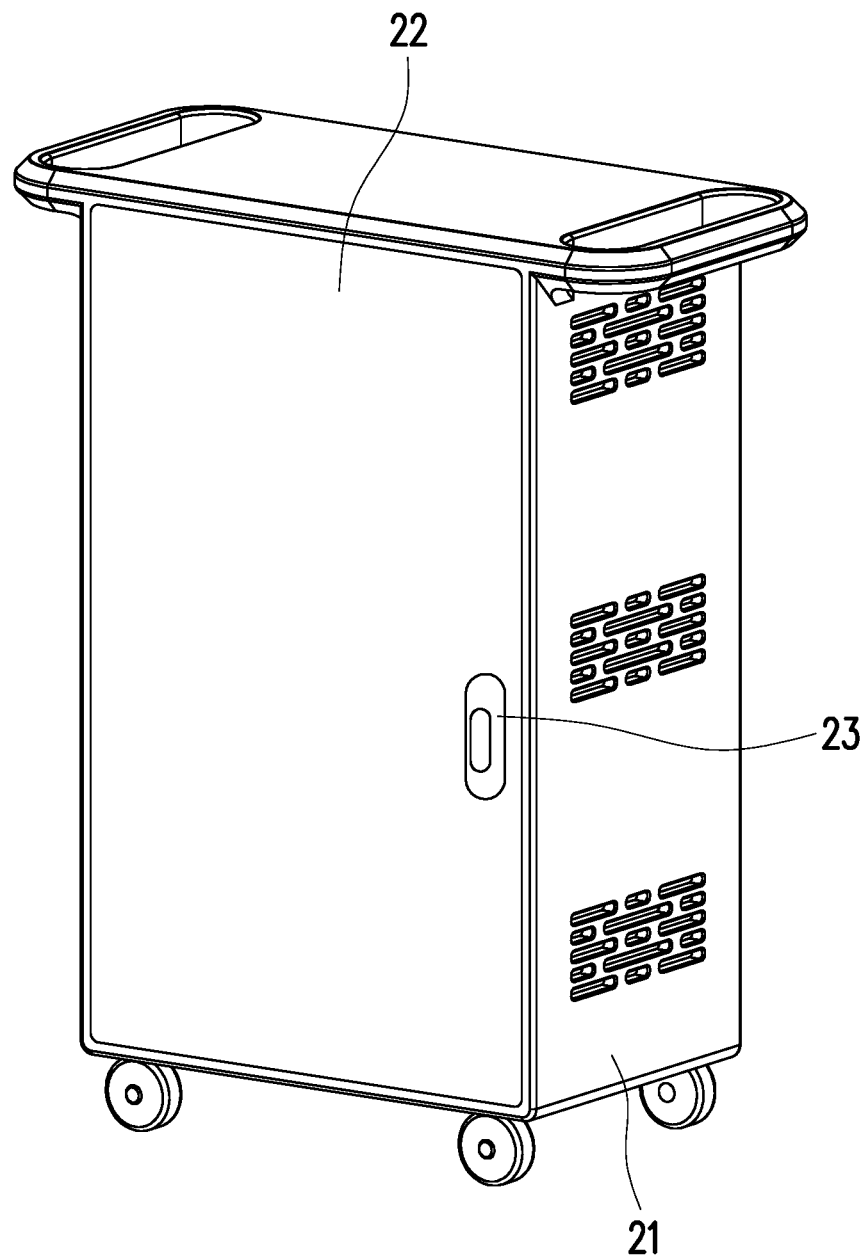
FIG. 7D is a schematic view of a sterilization apparatus according to an embodiment of the disclosure in a state where a door is closed.

FIG. 7A and FIG. 7B are schematic views of a sterilization apparatus according to an embodiment of the disclosure in a state where a door is open. FIG. 7C is a schematic view of a sterilization apparatus according to an embodiment of the disclosure in a state where a door is not completely closed. FIG. 7D is a schematic view of a sterilization apparatus according to an embodiment of the disclosure in a state where a door is closed. Referring to FIG. 7A and FIG. 7B, a sterilization apparatus 20 may adopt any one of the carrier 100 to the carrier 100E or a combination of at least two of the carrier 100 to the carrier 100E according to the embodiments. The carrier 100 is used for description in the following, but is not limited thereto.

In this embodiment, the sterilization apparatus 20 includes a cabinet 21 and at least one carrier 100, and the carrier 100 is slidably disposed in the cabinet 21 for the user to push and pull. As shown in FIG. 7B to FIG. 7D, the sterilization apparatus 20 further includes a door panel 22 rotatably connected to the cabinet 21. After the portable electronic device 10 is installed and positioned on the carrier 100 (as shown in FIG. 7B), the user may push the carrier 100 into the cabinet 21 and close an external opening of the cabinet 21 by rotating the door panel 22 (as shown in FIG. 7D).

Referring to FIG. 1B, FIG. 1C and FIG. 7A, the carrier 100 integrates an auto-sensing sterilization mechanism, and is mainly composed of the sterilization light sources 140 and the pressure sensors 150. Specifically, one of the sterilization light sources 140 is provided between any two of the pressure sensors 150 adjacent to each other, and they are disposed in groups. When the portable electronic device 10 is put into any one of the positioning spaces 101 and the pressure sensor 150 located in the positioning space 101 senses a pressure from the portable electronic device 10, the sterilization light source 140 adjacent to or closest to the pressure sensor 150 switches to a preparatory starting status. The preparatory starting status means that a controller or a processor (not shown) disposed in the cabinet 21 receives a signal from the pressure sensor 150 and determines a position of the portable electronic device 10 on the carrier 100, later, when the controller or the processor (not shown) receives a trigger signal, a specific one of the sterilization light sources 140 will be activated immediately (for example: the sterilization light source 140 closest to the portable electronic device 10) to emit a sterilization light L, rather than all the sterilization light sources 140 will be activated immediately when the portable electronic device 10 is placed on the carrier 100.

After the carrier 100 is moved into the cabinet 21, once the door panel 22 is locked to the cabinet 21, the trigger signal is immediately generated, as shown in FIG. 7D. On the contrary, as long as the door panel 22 is not completely locked to the cabinet 21, as shown in FIG. 7C, the controller or the processor (not shown) is in a state of not receiving the trigger signal, and the sterilization light source 140 will not be activated.

Referring to FIG. 7C and FIG. 7D, the sterilization apparatus 20 further includes a door lock 23 disposed on the door panel 22, and the door lock 23 may be an electronic lock to lock the door panel 22 to the cabinet 21 or release locking relationship between the door panel 22 and the cabinet 21. Furthermore, the door lock 23 and the sterilization light source 140 are electrically coupled to the controller or the processor (not shown) disposed in the cabinet 21. Once the door lock 23 locks the door panel 22 to the cabinet 21, the door lock 23 immediately sends the trigger signal to the controller or the processor (not shown), and the controller or the processor (not shown) immediately activates the sterilization light source 140. Once the door lock 23 releases the locking relationship between the door panel 22 and the cabinet 21, the door lock 23 immediately sends a closing signal to the controller or the processor (not shown), and the controller or the processor (not shown) immediately turns off the sterilization light source 140.

In another embodiment, the door panel 22 is pivotally connected to the cabinet 21 through a hinge (not shown). The hinge (not shown) is correspondingly provided with a sensor (not shown), and the sensor (not shown) and the sterilization light source 140 are electrically coupled to the controller or the processor (not shown). When the door panel 22 closes the external opening of the cabinet 21, the sensor (not shown) senses that an opening and closing angle of the door panel 22 is 0 degrees, and sends the trigger signal to the controller or the processor (not shown), and the controller or the processor (not shown) immediately activates the sterilization light source 140. Once the sensor senses that the opening and closing angle of the door panel 22 is greater than 0 degrees, the sensor immediately sends a closing signal to the controller or the processor (not shown), and the controller or the processor (not shown) immediately turns off the sterilization light source 140.

In summary, in the sterilization apparatus of the disclosure, the carrier has multiple positioning spaces arranged alternately for carrying and positioning multiple portable electronic devices, so that each part of each of the portable electronic devices may be completely sterilized. In addition, the carrier integrates an auto-sensing sterilization mechanism, which can sense the position of the each of the portable electronic devices on the carrier, and control a specific sterilization light source (for example: the sterilization light source closest to the portable electronic device) to enter the preparatory starting status. Once the sterilization apparatus switches from an on state to an off state, the specific sterilization light source is immediately started. Therefore, the sterilization apparatus of the disclosure not only has excellent flexibility in terms of operation, but also improves sterilization effectiveness and saves energy. In addition, the auto-sensing sterilization mechanism can prevent the sterilization light emitted by the sterilization light source from irradiating the surrounding personnel, thereby improving safety in terms of operation.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A sterilization apparatus for a portable electronic device, comprising:
   a cabinet; and
   at least one carrier, wherein the carrier comprises:
   a base slidably disposed on the cabinet and configured to carry at least one portable electronic device;
   a plurality of first positioning elements disposed in parallel on the base;
   a plurality of second positioning elements disposed in parallel on the base, wherein one of the second positioning elements is disposed between any two of the first positioning elements adjacent to each other, and any one of the first positioning elements is separated from any one of the second positioning elements by a positioning space;
   a plurality of sterilization light sources disposed correspondingly to the second positioning elements; and
   a plurality of pressure sensors disposed in parallel in the base, wherein the pressure sensors are respectively located in the positioning spaces, and one of the sterilization light sources is disposed between any two of the pressure sensors adjacent to each other,
   wherein when the portable electronic device is put into any one of the positioning spaces, and the pressure sensor located in the positioning space senses a pressure from the portable electronic device, the sterilization light source adjacent to the pressure sensor switches to a preparatory starting status.

2. The sterilization apparatus for a portable electronic device according to claim 1, wherein a height of each of the first positioning elements is lower than a height of each of the second positioning elements.

3. The sterilization apparatus for a portable electronic device according to claim 1, wherein each of the second positioning elements comprises a substrate connected to the base and a light transmitting cover disposed on the substrate, and the sterilization light sources are respectively disposed on the substrates and are respectively covered by the light transmitting covers.

4. The sterilization apparatus for a portable electronic device according to in claim 1, wherein each of the second positioning elements comprises a substrate connected to the base and a light transmitting plate disposed on the substrate, and the sterilization light sources are respectively disposed on the substrates and are respectively clamped between the light transmitting plates and the substrates.

5. The sterilization apparatus for a portable electronic device according to claim 4, wherein the substrate of the each of the second positioning elements has a groove, and the sterilization light source and the light transmitting plate are disposed in the groove.

6. The sterilization apparatus for a portable electronic device according to claim 4, wherein a top end of the light transmitting plate of the each of the second positioning elements is lower than or a same height as a top end of the substrate.

7. The sterilization apparatus for a portable electronic device according to claim 4, wherein a top end of the light transmitting plate of the each of the second positioning elements is higher than a top end of the substrate and a top end of the sterilization light source.

8. The sterilization apparatus for a portable electronic device according to claim 1, wherein each of the second positioning elements comprises a substrate connected to the base and a light transmitting plate disposed on the substrate, and the sterilization light source is disposed on a top end of the light transmitting plate.

9. The sterilization apparatus for a portable electronic device according to claim 1, wherein each of the sterilization light sources is disposed on a side of a corresponding second positioning element far away from the base, and a top end of the each of the sterilization light sources is a same height as or higher than a top end of the corresponding second positioning element.

10. The sterilization apparatus for a portable electronic device according to claim 1, wherein each of the second positioning elements comprises a connecting portion connected to the base and a positioning portion connected to the connecting portion, and the positioning portion of the each of the second positioning elements is suspended on the base, wherein the sterilization light sources are disposed on the base, and orthographic projection of the positioning portions of the second positioning elements on the base respectively overlaps the sterilization light sources.

11. The sterilization apparatus for a portable electronic device according to claim 10, wherein the base comprises a main body portion and a light transmitting portion disposed on the main body portion, the connecting portion of the each of the second positioning elements is connected to the main body portion, the first positioning elements are disposed in parallel on the light transmitting portion, and the sterilization light sources are disposed in the main body portion and covered by the light transmitting portion.

12. The sterilization apparatus for a portable electronic device according to claim 1 further comprising a door panel, wherein the door panel is movably connected to the cabinet, and when the carrier is moved into the cabinet and the door panel is locked in the cabinet, the sterilization light source in the preparatory starting status is activated to emit a sterilization light.

* * * * *